(12) United States Patent
Mac-Thiong et al.

(10) Patent No.: US 6,342,056 B1
(45) Date of Patent: Jan. 29, 2002

(54) SURGICAL DRILL GUIDE AND METHOD FOR USING THE SAME

(76) Inventors: Jean-Marc Mac-Thiong, 5901 McLynn, Montreal, Quebec (CA), H3X 2R3; Hubert Labelle, 11970 Beau Bois, Montreal (CA), H4K 2Y6

( * ) Notice: Subject to any disclaimer, the term of this patent is extended or adjusted under 35 U.S.C. 154(b) by 0 days.

(21) Appl. No.: 09/497,657

(22) Filed: Feb. 4, 2000

(51) Int. Cl.7 .............................................. A61B 17/58
(52) U.S. Cl. ............................. 606/96; 606/88; 606/103
(58) Field of Search ............................. 606/87, 73, 80, 606/96, 103, 86, 81, 88, 98, 179

(56) References Cited

U.S. PATENT DOCUMENTS

| | | | | |
|---|---|---|---|---|
| 4,672,957 A | * | 6/1987 | Hourahane ................... | 606/96 |
| 4,883,048 A | * | 11/1989 | Purnell et al. ................ | 606/96 |
| 4,907,577 A | | 3/1990 | Wu | |
| 5,163,940 A | * | 11/1992 | Bourque ....................... | 606/96 |
| 5,562,664 A | * | 10/1996 | Durlacher et al. ............ | 606/96 |
| 5,688,284 A | * | 11/1997 | Chervitz et al. .............. | 606/96 |
| 6,120,511 A | * | 9/2000 | Chan ............................ | 606/96 |

* cited by examiner

Primary Examiner—Pedro Philogene
(74) Attorney, Agent, or Firm—Swabey Ogilvy Renault; Robert Mitchell

(57) ABSTRACT

A surgical guiding instrument for use with a drilling tool and a bone engaging element, comprises a support on which the bone engaging element is adapted to be mounted for engaging a region of a bone to orient the support with respect thereto. The guiding instrument further includes a drill guide mounted to the support and defining a passage for guiding the drilling tool so as to prevent deviation of the drilling direction. The drill guide can be angularly adjusted relative to the bone engaging element in the plane of the support by simply sliding the drill guide on an arc of circle defined by the support.

15 Claims, 6 Drawing Sheets

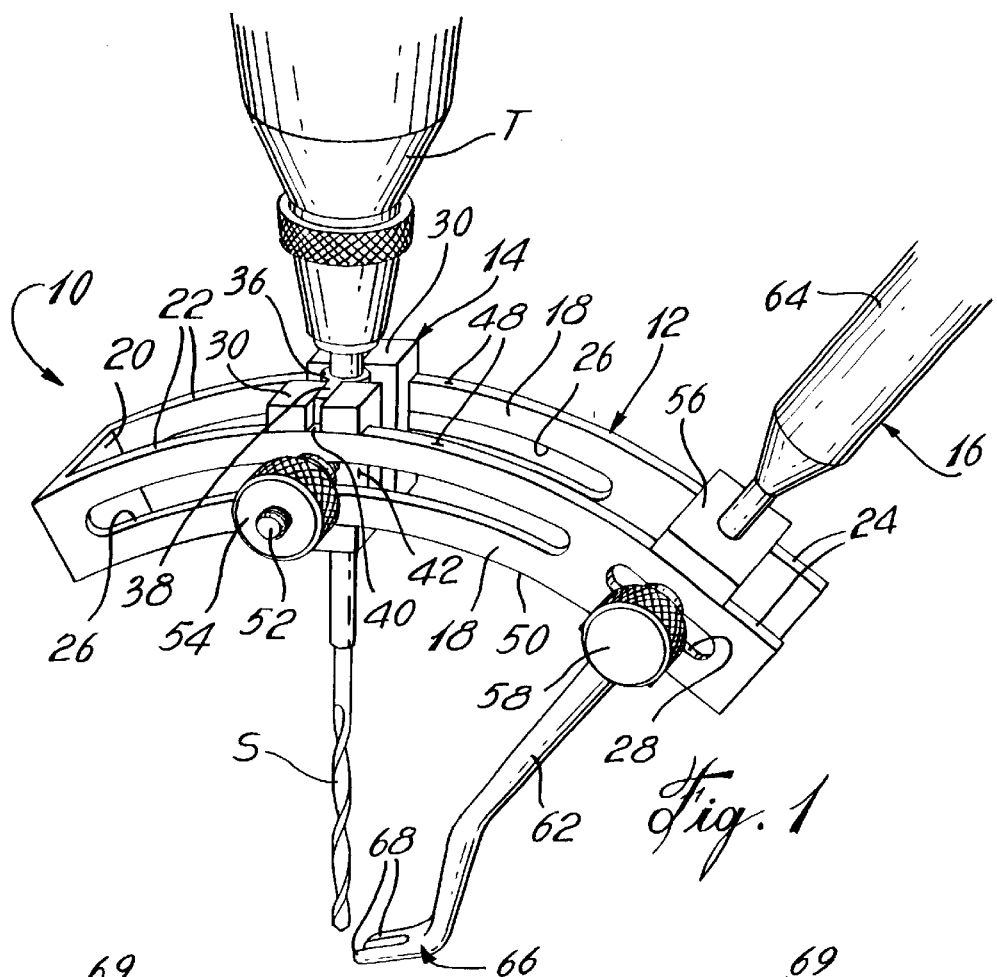
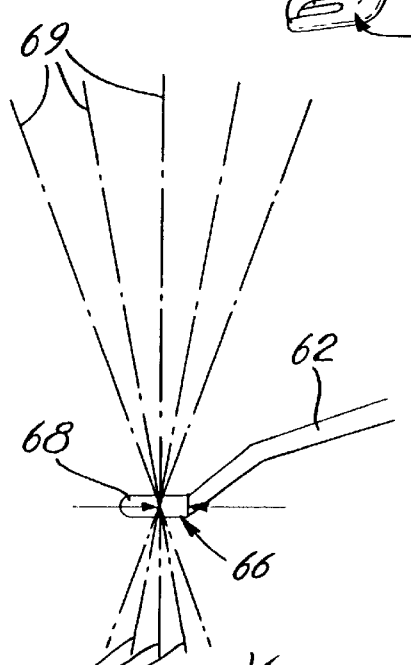
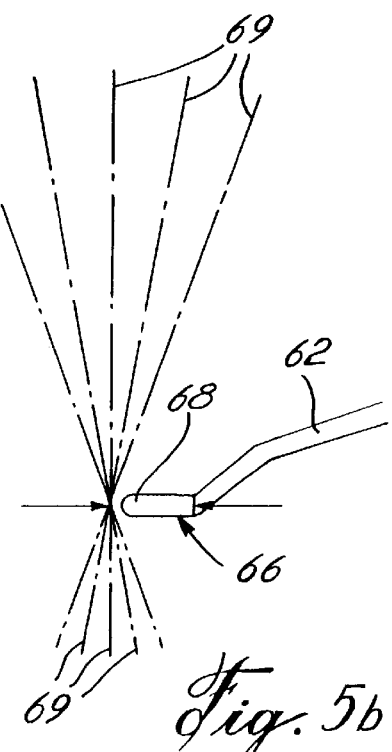

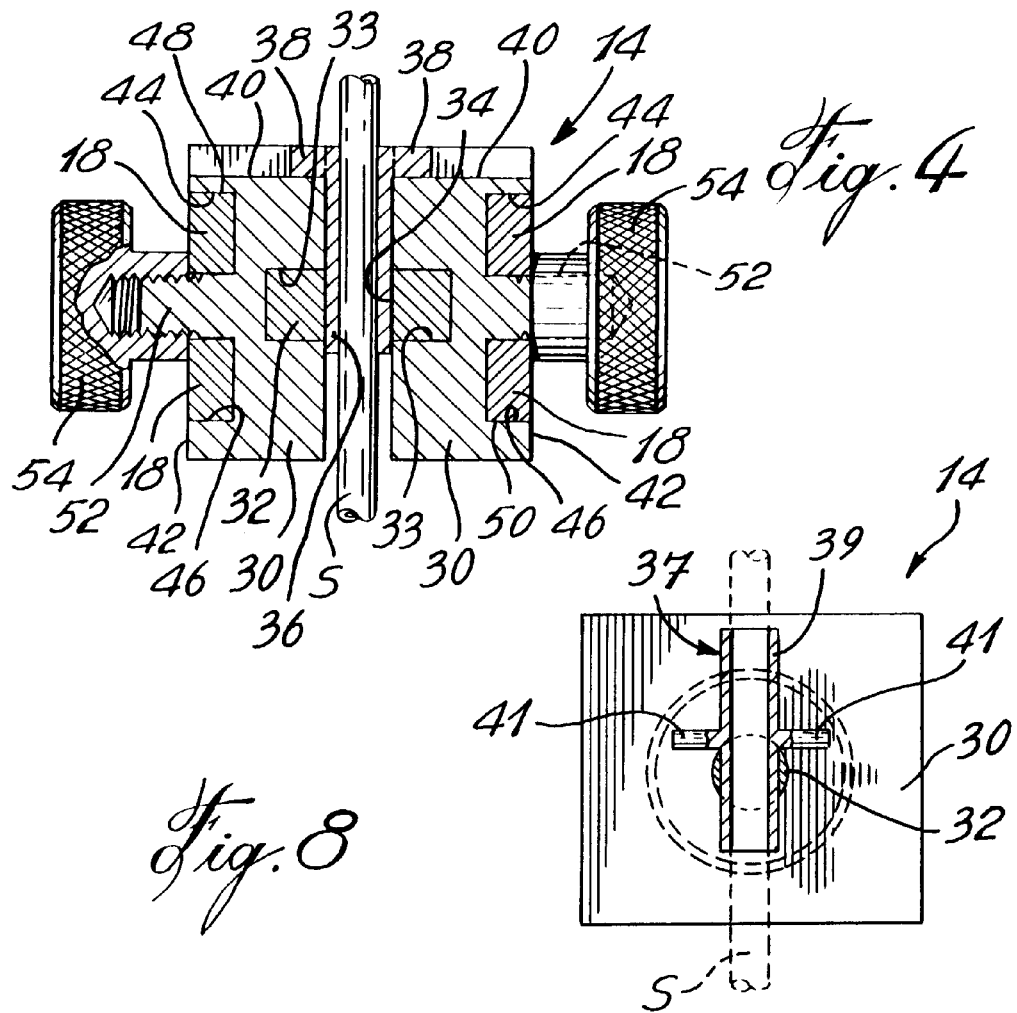
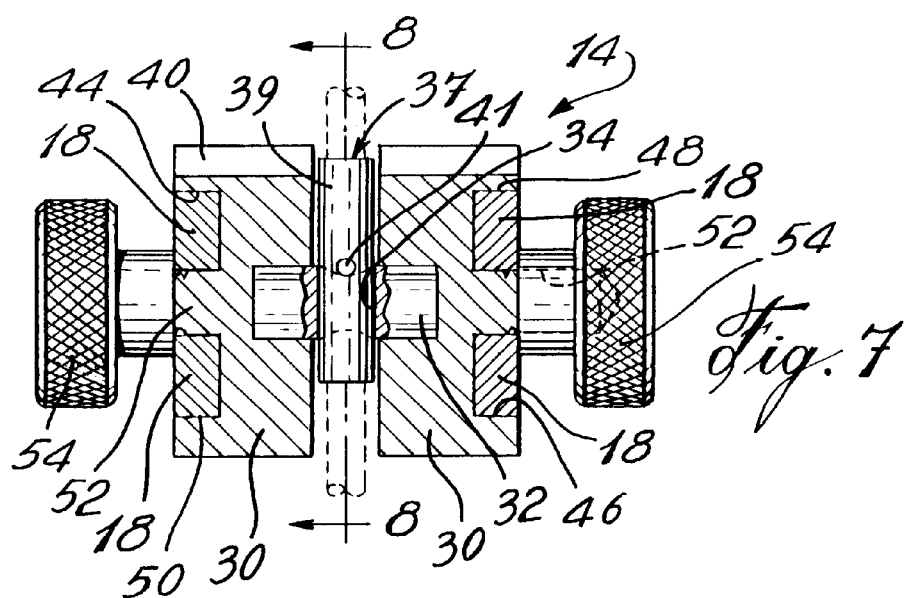

SURGICAL DRILL GUIDE AND METHOD FOR USING THE SAME

BACKGROUND OF THE INVENTION

1. Field of the Invention

The present invention relates to surgical instrumentation and, more particularly, pertains to a surgical instrument and a method for positioning and guiding a drilling tool.

2. Description of the Prior Art

It is well known to drill holes in bones in order to accommodate fastening devices used to anchor implants within a patient's body. For instance, over the last few years, pedicle screws have been used to anchor internal instrumentation systems to the spinal column of patients for correcting a variety of spinal disorders. There are many advantages of using such pedicles screw as compared to conventional anchoring devices, such as hooks, but the risks associated with their implantation into the vertebral column of the patients have limited their universal acceptance.

Commonly used technique for inserting a pedicle screw requires the preparation of a pilot hole through the pedicle before inserting the screw therein. Typically, the selection of the insertion point is made from anatomical techniques or a preoperative CT scan. The preoperative CT scan can be used for determining the angle of insertion, as well as for screw length and diameter. It is also known to use intra-operative X-rays or fluoroscopic guidance before pedicle hole preparation to assess the appropriate size and placement of the pedicle screws. After an appropriate pedicle has been selected, an initial small puncture through the posterior cortex can be made to mark the insertion point and to facilitate the drilling procedure. Then, the pilot hole is usually made with a drill bit or a pedicle probe. Before inserting the screw in the pilot hole, the latter is manually probed in order to check for violation of the pedicle walls. It is noted that the screw length can be determined by the use of a calibrated probe inserted into the pedicle pilot hole. Intra-operative X-rays or fluoroscopy can be used to verify the accuracy of the pilot hole or the screw.

It is also known to form individual templates customized on the basis of three-dimensional reconstruction of the bone structure extracted from CT image data in order to provide preoperative surgical planning.

Electrical methods and saline injection technique have been developed to confirm the correct path of the pilot hole prior to pedicle screw insertion.

Computer-assisted guidance systems have also been developed in order to visually track the intra-operative position of the vertebra during pedicle screw insertion.

In a further attempt to prevent misplacement of the pedicle screws, it has been proposed to use a guide to provide a safe route for drilling a pilot hole. U.S. Pat. No. 4,907,577 issued on Mar. 13, 1990 to Wu discloses a spinal transpedicle drill guide having a I-shaped body, a guiding base and a positioning base which are slidable in a transversal direction on the I-shaped body to prevent deviation of the drilling direction in the transversal plane of the vertebra of the pedicle. However, this guide does not allow for adjustment of the drilling path in the lateral plane of the vertebra.

SUMMARY OF THE INVENTION

It is therefore an aim of the present invention to provide a surgical guiding instrument which can be used to properly orient a drilling axis.

It is also an aim of the present invention to provide a surgical guiding instrument which is adapted to allow for safe insertion of a screw into a bone.

It is a further aim of the present invention to provide a surgical guiding instrument which is relatively simple and economical to manufacture.

It is a still further aim of the present invention to provide a kit adapted to orient and guide a drilling tool relative to a bone of a patient.

It is still a further aim of the present invention to provide a method for safely preparing a pilot hole in a pedicle of a selected vertebra of a patient's spinal column.

Therefore, in accordance with the present invention there is provided a surgical guiding instrument for use with a drilling tool, comprising a support, a bone engaging element adapted to be mounted on said support and having a tip portion for engaging a region of a bone to hold the support in a specific orientation with respect thereto, a drill guide mounted to said support and having a passage defining a drilling axis extending by the tip portion of said bone engaging element in a non-intersecting manner in the plane of said support so as to define a gap, at least one of said drill guide and said bone engaging element being adjustably movable relative to said support to provide for the increase or reduction of said gap in accordance with a diameter of the bone at a section thereof to be engaged by said bone engaging element.

In accordance with a further general aspect of the present invention, there is provided a kit for orienting and guiding a drilling tool relative to a patient's bone, comprising a support, a bone engaging element adapted to be mounted on said support for engaging a region of a bone to orient the support with respect thereto, and a drill guide adapted to be mounted to said support and defining a passage for guiding said drilling tool along a drilling axis during use, said drill guide being angularly adjustable relative to said bone engaging element in the plane of said support, thereby providing for adjustment of the angular orientation of the drilling axis in the plane of the support, and wherein said drill guide is adjustably rotatable about an axis of rotation perpendicular to said drilling axis, In accordance with still a further general aspect of the present invention, there is a method for preparing a pedicle pilot hole in a pedicle of a selected vertebra with a drill positioning guide having an elongated support on which a pedicle finder and a drill guide are mounted, wherein the drill guide defines a drilling axis extending by the tip portion of said pedicle finder in a non-intersecting manner in the plane of the support so as to define a gap, the method comprising the steps of a) adjusting the gap in accordance with the diameter of the pedicle in which a pilot hole has to be defined, b) engaging the tip portion of the pedicle finder with the pedicle in order to angularly align the support and the drill guide with the pedicle in a transversal plane of the vertebra, c) adjusting the position of the drill guide on the support so that the drilling axis be aligned with a predetermined insertion point on a posterior surface of the pedicle in order to angularly align the support and the drill guide with the pedicle in a lateral plane of the selected vertebra, and d) drilling the pedicle pilot hole in the pedicle with the drilling tool extending through the drill guide along the drilling axis thereof.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is perspective view of a surgical guiding instrument used in connection with a pedicle finder to guide a drilling tool in accordance with a first embodiment of the present invention;

FIG. 4 is a cross-sectional view taken along line 4—4 in FIG. 3;

FIGS. 5a and 5b are schematic views illustrating possible drilling paths for two different positions of the pedicle finder relative to the surgical guiding instrument;

FIG. 7 is a cross-sectional view taken along line 7—7 in FIG. 6;

FIG. 8 is a cross-sectional view taken along line 8—8 in FIG. 7;

DESCRIPTION OF THE PREFERRED EMBODIMENTS

Figure 2:
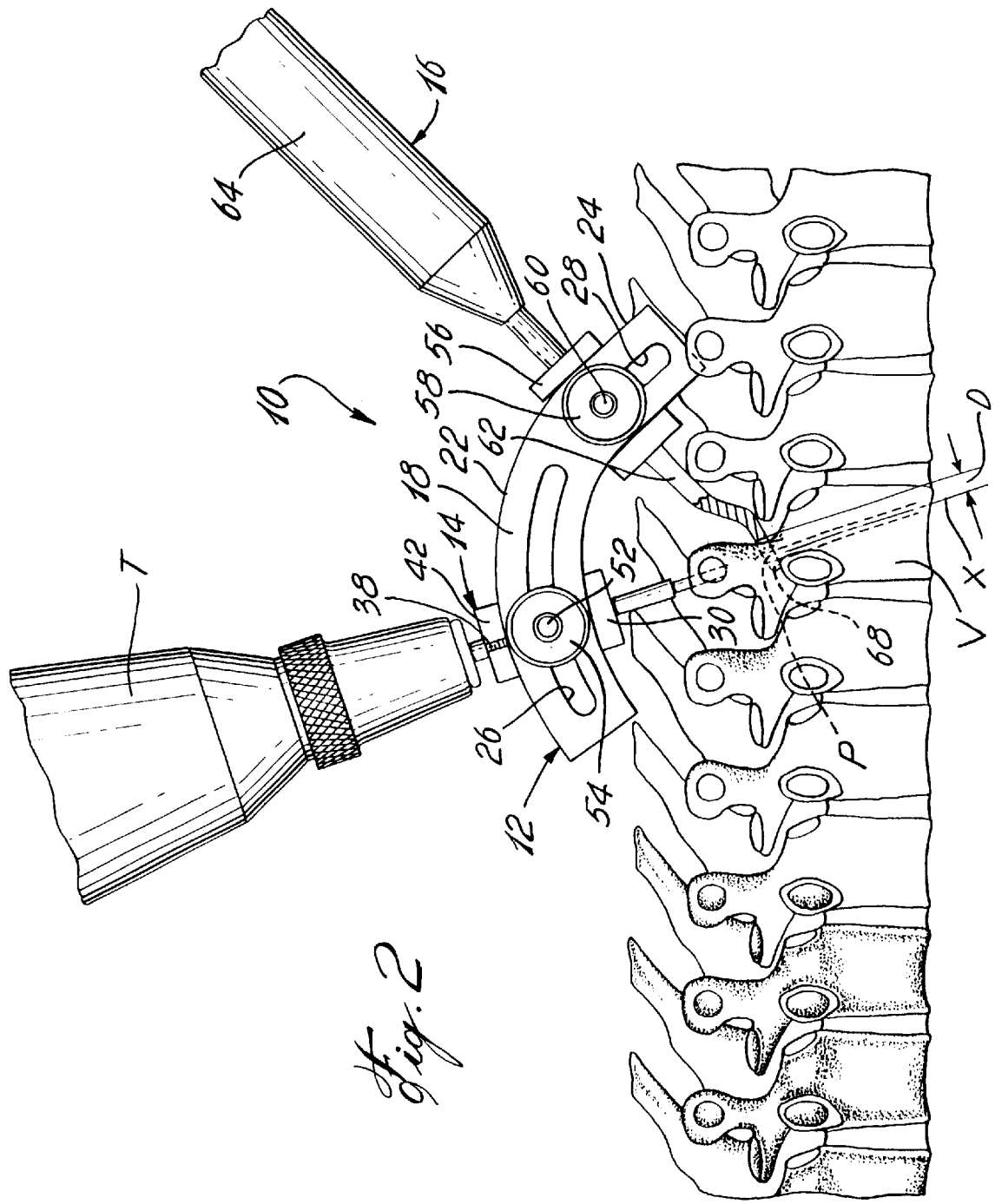
FIG. 2 is a lateral view of a portion of a spinal column illustrating how the surgical guiding instrument is used to guide the drilling tool in order to drill a pilot hole in a pedicle of a selected vertebra.

Now referring to the drawings and in particular to FIG. 1, a surgical guiding instrument 10 suited for ensuring precise drilling of a pedicle pilot hole prior to pedicle screw insertion will be described.

Figure 3:
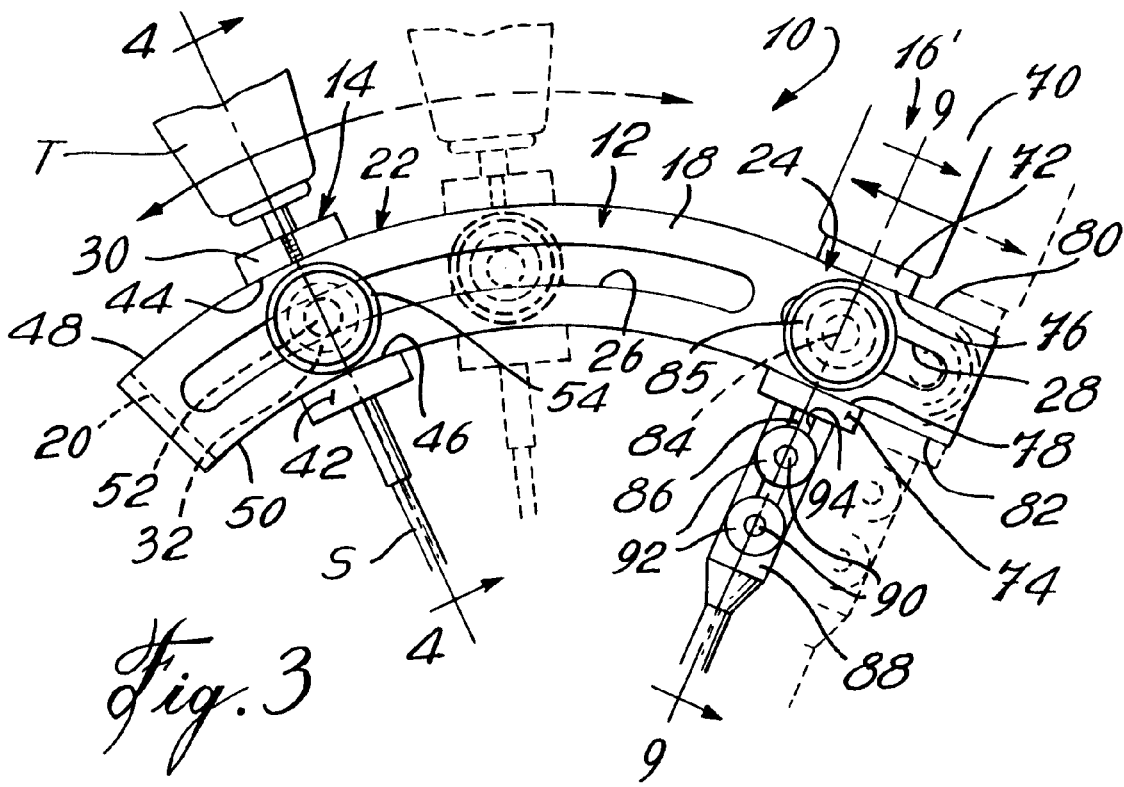
FIG. 3 is a side elevational view of the surgical guiding instrument.

The surgical guiding instrument 10 generally comprises a support 12 adapted to support a drill guide 14 and a pedicle finder 16. As seen in FIG. 3, the drill guide 14 and the pedicle finder 16 are both slidably displaceable on the support 12 and releasably securable at selected fixed positions thereon. The drill guide 14 defines a passage for guiding a drilling tool T during use. As seen in FIG. 2, the pedicle finder 16 is used to locate a pedicle P of a selected vertebra V and to properly position the support 12 with respect thereto. As will be explained hereinbelow, the engagement of the pedicle finder 16 with the pedicle P automatically ensures alignment of the passage defined by the drill guide 14 with the axis of the pedicle P in the transversal plane of the selected vertebra V, thereby providing proper angular orientation of the drilling tool T in the transversal plane of the vertebra V.

More specifically, as seen in FIG. 1, the support 12 includes a pair of similar parallel sliding rails 18 extending integrally at right angles from opposed sides of a transversal spacer 20. Each rail 18 is provided in the form of a flat elongated blade having a curvilinear proximal segment or portion 22 on which the drill guide 14 can be slidably displaced and a rectilinear distal end segment or portion 24 on which the pedicle finder 16 can be slidably displaced.

According to the illustrated embodiment, the rectilinear distal end portion 24 is tangential to the curvilinear proximal portion 22. The curvilinear proximal portion 22 of each rail 18 defines an elongated curved slot 26 which extends along an arc of circle which has the same center as the arc of circle described by the curvilinear proximal portion 22. The rectilinear distal end portion 24 of each rail 18 defines an elongated rectilinear slot 28.

As seen in FIG. 4, the drill guide 14 includes a pair of identical spaced-apart rail engaging members 30 connected to each other via a sleeve support 32 extending transversally therebetween. The sleeve support 32 has a cylindrical shape and is mounted at opposed ends thereof into cylindrical recesses 33 defined in respective inner sides of the rail engaging members 30 in a manner so as to allow the sleeve support 32 to rotate with respect to the rail engaging members 30 about a central longitudinal axis of the sleeve support 32.

The sleeve support 32 has a transversal bore 34 extending therethrough substantially mid-way between the opposed ends thereof. Depending whether it is desired to block the rotational movement of the sleeve support 32 relative to the rail engaging members 30, a first or a second type of guiding sleeve is removably inserted through the transversal bore 34 for guiding the drilling tool T during use. For instance, when it is desired to prevent rotational movement between the sleeve support 32 and the rail engaging members 30, the guiding sleeve illustrated at 36 in FIGS. 1 to 4 can be used.

As seen in FIGS. 1 to 4, the guiding sleeve 36 has a cylindrical tubular shape and has an external diameter which is slightly less than the diameter of the transversal bore 34 to allow the same to be readily inserted therethrough between the rail engaging members 30 in order to subsequently receive the shank S of the drilling tool T and guide the same in a diametrical direction relative to the arc of circle described by the support 12. The guiding sleeve 36 is provided at an upper end thereof with a pair of diametrically opposed lateral locking members 38 which are sized and configured to be slidably lowered in a corresponding pairs of transversal slots 40 defined in respective top surfaces of the rail engaging members 30. Once in position, the locking members 38 will support the guiding sleeve 36 on the rail engaging members 30 while preventing relative rotational movement between the sleeve support 32 and the rail engaging members 30.

Figure 6:
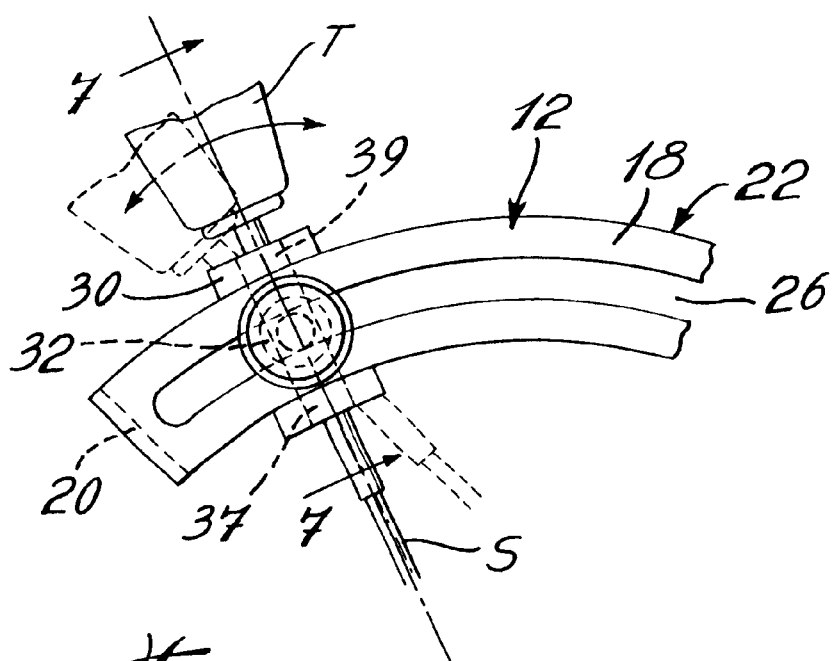
FIG. 6 is an enlarged elevational view of the surgical guiding instrument illustrating a variant of the present invention wherein the guiding sleeve used to guide the drilling tool is freely rotatable in the plane of the surgical guiding instrument.

If it is desired to allow the sleeve support 32 to freely rotate relative to the rail engaging members 30, as seen in FIG. 6, a second type of guiding sleeve, such as the one designated by reference numeral 37 in FIGS. 7 and 8, can be used. The guiding sleeve 37 includes an elongated cylindrical tubular body 39 sized to be removably insertable within the transversal bore 34. A pair of diametrically opposed support members 41 extend laterally outwardly from the tubular body 39 mid-way between the opposed ends thereof. The guiding sleeve 37 is inserted within the transversal bore 34 with the support members 41 extending in a direction parallel to the sliding rails 18 down to a position wherein the support members 41 abut against the top surface of the sleeve support 32.

As seen in FIGS. 1 and 4, each rail engaging member 30 has a recessed C-shaped outer surface 42 defining first and second spaced-apart curvilinear running surfaces 44 and 46 respectively adapted to be slidably engaged with top and bottom curvilinear surfaces 48 and 50 of one of the sliding rails 18. The distance separating the rail engaging members 30 is such as to allow the same to be inserted between the rails 18 with respective first and second curvilinear running surfaces 44 and 46 thereof slidably engaged with the associated sliding rails 18, thereby ensuring proper support of the drill guide 14 on the support 12.

As best seen in FIG. 4, a threaded pin 52 extends integrally laterally outwardly of the outer surface of each rail engaging member 30 between the first and second running surfaces 44 and 46 thereof to extend through the elongated curvilinear slot 26 of the corresponding sliding rail 18 of the support 12. A nut 54 is threadably engaged on the free distal end of each threaded pin 52 laterally outwardly of the sliding rails 18 in order to releasably lock the drill guide 14 in a desired position on the support 12.

The pedicle finder 16 may consist of any available or conventional pedicle finder or, alternatively, may be sold with the support 12 and the drill guide 14 in the form of a kit. When a conventional pedicle finder is used, as seen in FIGS. 1 and 2, a carrier 56, which is adapted to releasably clamp the pedicle finder 16, is slidably mounted to respective rectilinear distal end portions 24 of the rails 18 in a manner similar to that of the drill guide 14. A nut 58 engaged on a threaded pin 60 (see FIG. 2) extending laterally outwardly from the carrier 56 and through an associated rectilinear elongated slot 28 can be tightened against the outer surface of the adjacent sliding rail 18 to releasably secure the carrier 56 in place on the support 12. As is well known in the art, the pedicle finder 16 includes a shank 62 extending from a handle 64 and having a tip end portion 66 which is bent away from the longitudinal axis thereof to engage the pedicle P. The tip end portion 66 includes a pair of spaced apart prong-like members 68 configured to receive therebetween a portion of the pedicle P of the selected vertebra V. It is noted that the pedicle finder 16 is secured to the carrier 56 with the tip end portion 66 thereof extending in parallel relative to the sliding rails 18 and with the longitudinal axis of the shank 62 extending at right angles relative to the rectilinear distal end portions 24 of the rails 18.

In use, the proper insertion point and orientation of the drilling tool T in the lateral plane of the selected vertebra (see FIG. 2) is first determined by anatomical knowledge as well as by preoperative imaging technique (radiographs or CT scan) routinely used. Then, the position of the pedicle axis (i.e. the axis of the projected pilot hole) X in the lateral plane of the vertebra V is determined, such as by conventional imaging technique. After having established the position of the pedicle axis X in the lateral plane, the distance D between the pedicle axis X and the inferior base of the pedicle P is calculated for the pedicle section that will be intersected by the pedicle finder 16, as seen in FIG. 2. It is noted that this distance could also be calculated directly from a postero-anterior view.

Once the distance D between the pedicle axis X and the inferior base of the pedicle P is determined, the surgical guiding instrument 10 is adjusted in order to obtain adequate position of the drilling tool T inside the pedicle P at the section intersected by the pedicle finder 16 More specifically, the surgical guiding instrument 10 is adjusted by slidably displacing the carrier 56 on the rectilinear distal end portions 24 of the sliding rails 18 and slidably displacing the pedicle finder 16 longitudinally with respect to the carrier 56 such that the perpendicular distance or gap between the root of the prong-like members 68 and the drilling axis 69 (see FIGS. 5$a$ and 5$b$) defined by the guiding sleeve 36 is equal to the distance D. The fact that the pedicle finder 16 is displaceable along two independent axes allows a precise adjustment of the gap between the drilling axis and the root of the prong-like members 68 of the pedicle finder 16.

As seen in FIGS. 5$a$ and 5$b$, the position of the carrier 56 on the sliding rails 18 can be adjusted for different distances $D_1$ and $D_2$ between the drilling axis 69 and the root of the prong-like members 68, and the angular orientation of the drilling axis 69 in the lateral plane of the vertebra V can be adjusted without changing these distances $D_1$ and $D_2$. Indeed, when moving the drill guide 14 along the curvilinear proximal portions 22 of the sliding rails 18, the distance $D_1$ and $D_2$ remain constant for all possible drilling paths. This is because the movement of the drill guide 14 on the rails 18 is restrained to an arc of circle.

Once the position of the pedicle finder 16 has been adjusted relative to the rails 18 and to the carrier 56 in accordance to the distance D, the surgeon holds the pedicle finder 16 with one hand to localize the pedicle P with the tip end portion 66 of the pedicle finder 16. More particularly, as seen in FIG. 2, the tip end portion 66 of the pedicle finder 16 is engaged with the pedicle P so as to tightly engage the prong-like members 68 with the opposed sides of the pedicle P and so as to abut the inferior base of the pedicle P with the root of the prong-like members 68, thereby placing the pedicle finder 16 in the same angular orientation as the pedicle P in the transversal plane of the selected vertebra V. This simultaneously place the guiding sleeve 36 in the same transversal orientation relative to the vertebra V, since the pedicle finder 16 and the drill guide 14 extend in the plane of the support 12 and are structurally interconnected thereby. This advantageously provides accurate angle of insertion of the drilling tool T in the transverse plane of the vertebra V, thereby reducing the risk of neurological complications due to misplacement of the pedicle screw (not shown) in the transverse plane of the vertebra V.

Thereafter, a guiding rod, which could be the shank S of the drilling tool T is inserted into the guiding sleeve 36. Then, while holding the pedicle finder 16 with one hand, the surgeon uses his other hand to slide the drill guide 14 on the rails 18 and secure the drill guide 14 to the rails 18 when the guiding rod is aligned with the predetermined insertion point on the posterior vertebral surface, thereby ensuring accurate angle of insertion of the drilling tool T in the lateral plane of the vertebra V and preventing misplacement of the pedicle screw (not shown) in the lateral plane of the selected vertebra V. Subsequently, the guiding rod is removed and the drilling tool is inserted in the guiding sleeve. It is understood that this step is not performed if the drilling tool T is used as the guiding rod, as mentioned hereinbefore. Finally, the drilling tool T is operated to drill the pedicle pilot hole.

If the guiding sleeve 37 (see FIGS. 7 and 8) is used in order to allow the drill guide 14 to rotate in the lateral plane of the vertebra V during use, then only the orientation of the drilling tool T in the transverse plane of the vertebra V can be provided by the surgical guiding instrument 10. The orientation of the surgical guiding instrument 10 in the lateral plane is determined solely by the surgeon and the use of either anatomical or imaging techniques.

Figure 9:
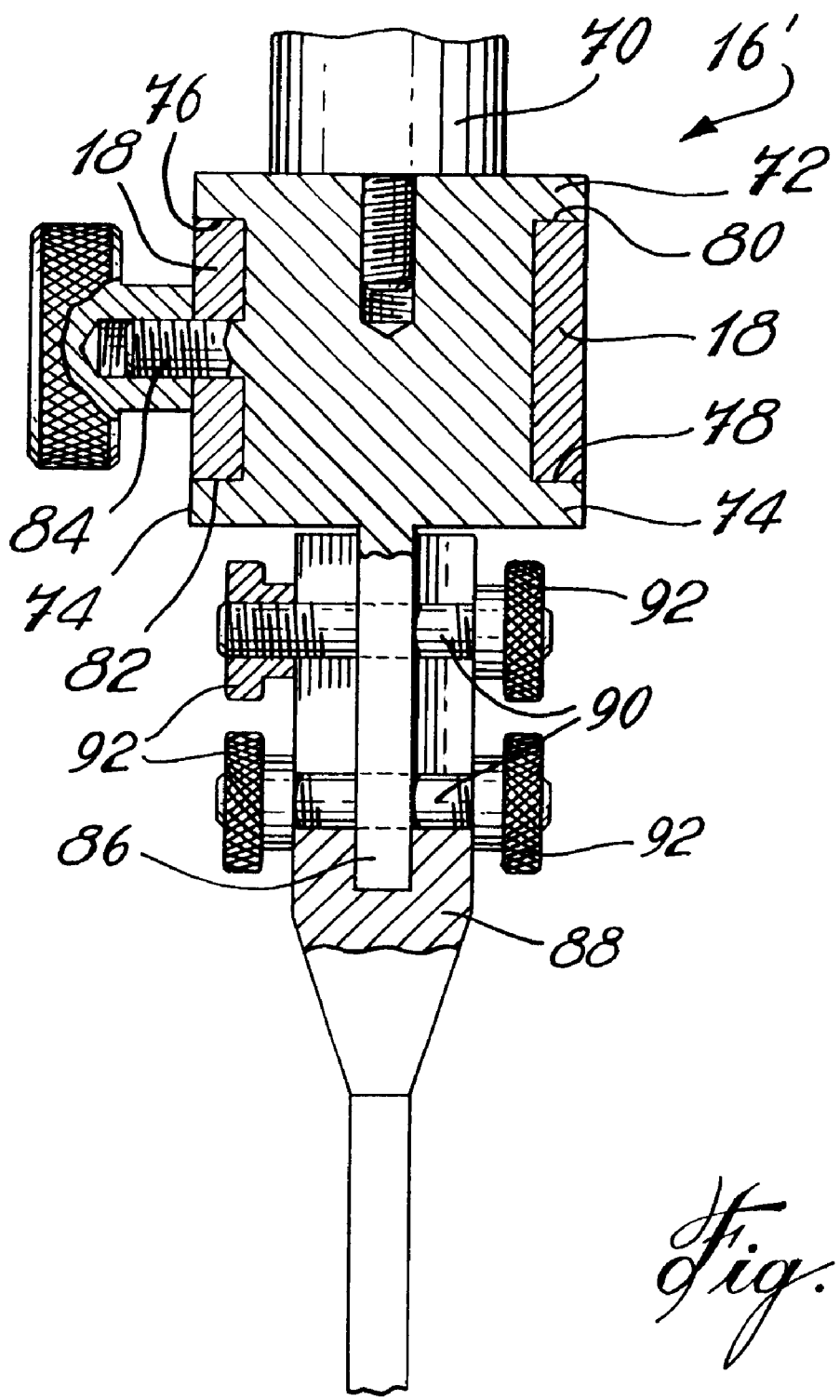
FIG. 9 is a cross-sectional view taken along line 9—9 in FIG. 3.

FIGS. 3 and 9 illustrate another construction of a pedicle finder 16' which has been specifically designed to be used in connection with the support 12. The pedicle finder 16' includes a handle 70 which is threadably mounted to the top surface of a mobile support 72 disposed between the rails 18 and having opposed outer recessed C-shaped side surfaces 74 slidably engaged with respective rails 18. Each outer recessed C-shaped side surface 74 has first and second linear running surfaces 76 and 78 adapted to be respectively slidably engaged with the top and bottom surfaces 80 and 82 of the rectilinear distal end portion 24 of the associated rail 18. A threaded pin 84 extends integrally laterally outwardly of at least one of the outer surface of the support 72 for engagement within the rectilinear slot 28 of the adjacent rail 18. A nut 85 is provided for releasably securing the support 72 in a selected position on the support 12, as described hereinbefore with respect to the drill guide 14 and the carrier 56. A first shank segment 86 extends integrally downwardly from the bottom surface of the support 72 and is adapted to be telescopically engaged with a second terminal shank segment 88, thereby allowing an adjustment of the length of the pedicle finder 16'. Two pairs of threaded pins 90 extend laterally outwardly from opposed sides of the first segment 86 to cooperate with two pairs of nuts 92 in order to releasably retain the first and second shank segments 86 and 88 in a desired axial relation. The second shank segment 88 is fitted over the first shank segment 86 with the threaded pins 90 extending through axial slots 94 (see FIG. 3) defined in opposed sides of the second shank segment 88, as seen in FIG. 9.

Figure 10:
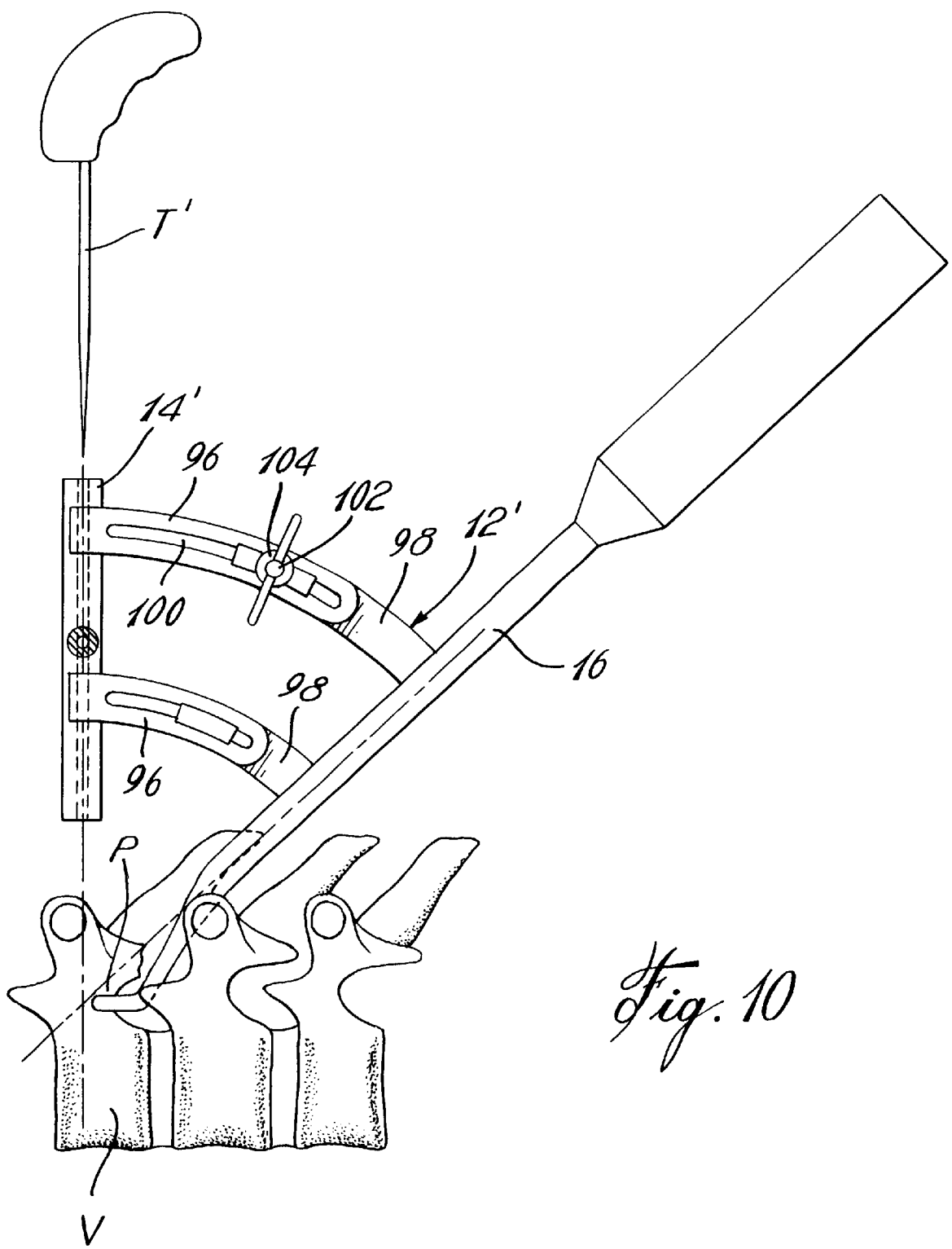
FIG. 10 is a schematic lateral elevational view of a second embodiment of the present invention.

FIG. 10 illustrates a second embodiment of the present invention wherein the support 12' is telescopic and the drill guide 14' and the pedicle finder 16 are fixedly mounted to the support 12'. The support 12' includes a first pair of curved segments 96 extending from one side of the drill guide 14' and a second pair of curved segments 98 telescopically interconnected at a first distal end portion thereof to a corresponding distal end portion of the first pair of curved segments 96. The other end of the second curved segments 98 are fixed to the pedicle finder 16. An elongated curved slot 100 is defined in one of the segments 96 to receive a threaded pin 102 extending laterally outwardly from adjacent segment 98. A nut 104 is threadably engaged on the threaded pin 102 to releasably retain the support 12' in a variety of positions between fully extended and contracted positions thereof.

It is also understood that the present invention can be used with a variety of drilling tools, such as those depicted by T and T' in FIGS. 1 and 10, respectively.

The present invention is advantageous in that it provides precise drilling of the pedicle pilot hole prior to pedicle screw insertion, thereby reducing the complications associated with misplaced pedicle screws. The present invention prevent deviation of the drilling direction so as to reduce the possibilities of injury during spinal surgery to the nerve root, spinal cord or nearby anatomic regions. The surgical guiding instrument 10 allows safe pedicle preparation by providing accurate angle of insertion of the drilling tool in transverse and lateral planes. Furthermore, the surgical guiding instrument ensures better precision, control and stability for the surgeon during the drilling process.

The surgical guiding instrument 10 also allows instantaneous correction in the orientation of the drilling when the vertebra V moves. This is because the pedicle finder 16 is always in contact with the pedicle P.

The present invention is also advantageous in that it avoids the use of invasive imaging technique (e.g. fluoroscopy) during pedicle screw insertion. Moreover, it avoids the use of expensive and time-consuming computer-assisted systems for pedicle screw insertion.

Finally, although the present invention has been described in the context of a spinal surgery, it is understood that the present invention could also be used in other applications, such as percutaneous drilling, drilling through cylindrical bones or through any bone region not readily visualized by the user.

What is claimed is:

1. A surgical guiding instrument for use with a drilling tool, comprising a support, a bone engaging element adapted to be mounted on said support and having a tip portion for engaging a region of a bone to hold the support in a specific orientation with respect thereto, a drill guide mounted to said support and having a passage defining a drilling axis extending by the tip portion of said bone engaging element in a non-intersecting manner in the plane of said support so as to define a gap, at least one of said drill guide and said bone engaging element being adjustably movable relative to said support to provide for the increase or reduction of said gap in accordance with a diameter of the bone at a section thereof to be engaged by said bone engaging element.

2. A surgical guiding instrument as defined in claim 1, wherein said support extends at least partly along an arc of circle, and wherein said drill guide is displaceable relative to the bone engaging element along said arc of circle with said passage thereof extending in a diametrical direction relative to said arc of circle.

3. A surgical guiding instrument as defined in claim 2, wherein said drill guide is displaceable on said support and releasably securable at selected fixed positions along said arc of circle.

4. A surgical guiding instrument as defined in claim 3, wherein said support has successive curvilinear and rectilinear segments, and wherein said drill guide is slidably displaceable on said curvilinear segment, whereas the bone engaging member is secured to a carrier which is slidably displaceable on said rectilinear segment and releasably securable at selected fixed positions thereon, said rectilinear segment being oriented relative to said curvilinear segment so as to provide translational movements of said bone engaging elements towards and away from said drilling axis to close and open said gap as a result of a movement of said carrier on said rectilinear segment.

5. A surgical guiding instrument as defined in claim 3, wherein said drill guide includes a sleeve support mounted for rotation about an axis of rotation perpendicular to said drilling axis, and first and second interchangeable guiding sleeves adapted to be selectively mounted to said sleeve support to guide the drilling tool, said first and second interchangeable guiding sleeves being respectively adapted to block and allow rotational movement of said sleeve support about said axis of rotation.

6. A surgical guiding instrument as defined in claim 5, wherein said sleeve support extend between a pair of runners slidably engaged with said support, and wherein said first guiding sleeve and said runners are provided with cooperating interlocking members.

7. A surgical guiding instrument as defined in claim 4, wherein said support includes a pair of parallel sliding rails on which said drill guide and said carrier are slidably mounted.

8. A kit for orienting and guiding a drilling tool relative to a patient's bone, comprising a support, a bone engaging element adapted to be mounted on said support for engaging a region of a bone to orient the support with respect thereto, and a drill guide adapted to be mounted to said support and defining a passage for guiding said drilling tool along a drilling axis during use, said drill guide being angularly adjustable relative to said bone engaging element in the plane of said support, thereby providing for adjustment of the angular orientation of the drilling axis in the plane of the support, and wherein said drill guide is adjustably rotatable about an axis of rotation perpendicular to said drilling axis.

9. A kit as defined in claim 8, wherein said support extends at least partly along an arc of circle, and wherein, when installed on said support, said drill guide is displaceable relative to said bone engaging element along said arc of circle with said passage thereof extending in a diametrical direction relative to said arc of circle.

10. A kit as defined in claim 9, wherein said drill guide is adapted to be displaceably mounted on said support and releasably secured at selected fixed positions along said arc of circle.

11. A kit as defined in claim 10, wherein said support has successive curvilinear and rectilinear segments, and wherein said drill guide is adapted to be slidably mounted on said curvilinear segment, whereas said bone engaging member is adapted to be slidably mounted on said rectilinear segment and releasably secured at selected fixed positions thereon.

12. A kit as defined in claim 11, wherein said bone engaging member includes a pedicle finder having a shank, said shank extending perpendicularly to said rectilinear segment when said pedicle finder is mounted to said support.

13. A kit as defined in claim 11, wherein said drill guide includes a sleeve support adapted to be mounted for rotation about said axis of rotation, and first and second interchangeable guiding sleeves adapted to be selectively mounted to said sleeve support to guide the drilling tool, said first and second interchangeable guiding sleeves being respectively adapted to block and allow rotational movement of said sleeve support about said axis of rotation.

14. A method for preparing a pedicle pilot hole in a pedicle of a selected vertebra with a drill positioning guide having an elongated support on which a pedicle finder and a drill guide are mounted, wherein the drill guide defines a drilling axis extending by a tip portion of said pedicle finder in a non-intersecting manner in the plane of the support so as to define a gap, the method comprising the steps of:

a) adjusting the gap in accordance with the diameter of the pedicle in which a pilot hole has to be defined, b) engaging the tip portion of the pedicle finder with the pedicle in order to angularly align the support and the drill guide with the pedicle in a transversal plane of the vertebra, c) adjusting the position of the drill guide on the support so that the drilling axis be aligned with a predetermined insertion point on a posterior surface of the pedicle in order to angularly align the support and the drill guide with the pedicle in a lateral plane of the selected vertebra, and d) drilling the pedicle pilot hole in the pedicle with the drilling tool extending through the drill guide along the drilling axis thereof.

15. A method as defined in claim 14, wherein step a) is effected by:

determining the distance D between an inferior base of the pedicle and a projected drilling axis in a lateral plane of the selected vertebra at a section of the pedicle intersected by the pedicle finder, and adjusting the position of the pedicle finder on the elongated support according to distance D.

* * * * *